United States Patent [19]

Ferrara

[11] Patent Number: 4,486,194
[45] Date of Patent: Dec. 4, 1984

[54] THERAPEUTIC DEVICE FOR ADMINISTERING MEDICAMENTS THROUGH THE SKIN

[76] Inventor: James Ferrara, 1 Armstrong Ave., Methuen, Mass. 01844

[21] Appl. No.: 502,212

[22] Filed: Jun. 8, 1983

[51] Int. Cl.³ .............................................. A61F 7/02
[52] U.S. Cl. .................................... 604/897; 604/308
[58] Field of Search ............... 604/896, 897, 289, 304, 604/306, 308; 128/156

[56] References Cited

U.S. PATENT DOCUMENTS

| 432,798 | 7/1890 | Hirst | 128/154 |
| 2,367,690 | 1/1945 | Purdy | 128/154 |
| 3,996,934 | 12/1976 | Zaffaroni | 128/268 |
| 4,023,569 | 5/1977 | Warnecke et al. | 128/154 |
| 4,341,208 | 7/1982 | Gordon | 128/268 |

Primary Examiner—Stephen C. Pellegrino
Assistant Examiner—Harrie S. Samaras
Attorney, Agent, or Firm—Edward A. Gordon

[57] ABSTRACT

A therapeutic device adapted to releasibly confine a quantity of therapeutic material therefrom to a recipient or environment of use and comprises a supporting member, means disposed in the supporting member to receive a therapeutic material, means for detecting when a predetermined amount of therapeutic material has been deposited within the receiving means and means for securing the device adjacent to the recipient or environment of use. The means for receiving the therapeutic material may comprise according to the invention a chamber, channels, or capsules. The means for detecting when a predetermined amount of therapeutic material has been deposited comprises indicia of measurement such as lines and numerals and spaced ridges or raised portions, the spaces between each of which represent a quantity of measurement. Attaching members are provided for securing the device and the therapeutic material adjacent the recipient and/or environment of use.

1 Claim, 8 Drawing Figures

4,486,194

THERAPEUTIC DEVICE FOR ADMINISTERING MEDICAMENTS THROUGH THE SKIN

FIELD OF THE INVENTION

This invention relates to a device for the administration of a theraputic medicament and more particularly to a theraputic device for application of a measured amount of a theraputic medicament to the skin of the recipient.

BACKGROUND OF THE INVENTION

Many medicaments are employed to prevent or control against the occurrence of a disease or disorder as opposed to those which are active against a disease or disorder only when it occurs. However, such medicaments, which are generally termed prophylactics, to be effective, need normally to be administered in low doses over a period of time, sometimes periodically also; and such a procedure is necessarily time consuming and inconvenient. The term therapeutic material or medicament, as that term is used in this specification and the appended claims, are agents such as medicines and drugs which, when applied to the skin or mucosa of the recipient or environment of use, are absorbed through the body surface to which applied and are transported from their site of application by the recipient's circulation system or lymphatic system, to cause a pharmacologic or physiologic response at a remote site in the body.

The prior art teaches a variety of devices for delivering a medicament to an enviroment of use. Such prior art devices are disclosed in U.S. Pat. Nos. 3,886,935; 3,996,934; 4,117,841; 4,026,290; 4,077,407 and 4,160,020, incorporated herein by reference; and others. While the prior art devices represent significant advancement in the art, it is desirable to provide for a new and improved therapeutic device which provides the unusual combinations and sub-combinations of advantages in construction, fabrication, mode of operation and adaptability and comfort in use.

It is also a desirable object of the invention to provide such a therapeutic device which provides indica of measurement whereby the user may quickly and easily measure a pre-determined amount of medicament to be received by the device.

It is also a desirable object to provide a therapeutic device which will easily enable the user to monitor the absorption of the therapeutic material and determine from time to time the amount of therapeutic material remaining.

A further desirable object of the invention is to provide a therapeutic device requiring relatively little cost to manufacture, thereby making it generally available and providing a clean, effective device for applying medicaments to an environment of use.

SUMMARY OF THE INVENTION

The invention comprises a therapeutic device adapted to releasibly confine a quantity of therapeutic material therefrom to a recipient or environment of use and comprises a supporting member, means disposed in said supporting member to receive a therapeutic material, means for detecting when a predetermined amount of therapeutic material has been disposed within the receiving means and means for securing the device adjacent to the recipient or environment of use. The means for receiving the therapeutic material may comprise according to the invention a chamber, channels, or capsules. In accordance with the invention, the means for detecting when a predetermined amount of therapeutic material has been disposed in the receiving means comprises indicia of measurement such as lines and numerals, and spaced ridges or raised portions, the space between which represents a quantity of measurement. Attaching members are provided for securing the device and the therapeutic material adjacent the recipient and/or environment of use.

BRIEF DESCRIPTION OF THE DRAWINGS

For a fuller understanding of the nature and desired objects of the inventions, reference should be made to the following detailed description taken in connection with the accompanying drawing wherein like reference characters refer to corresponding parts throughout the several views and wherein.

DETAILED DESCRIPTION OF THE INVENTION

Figure 1:
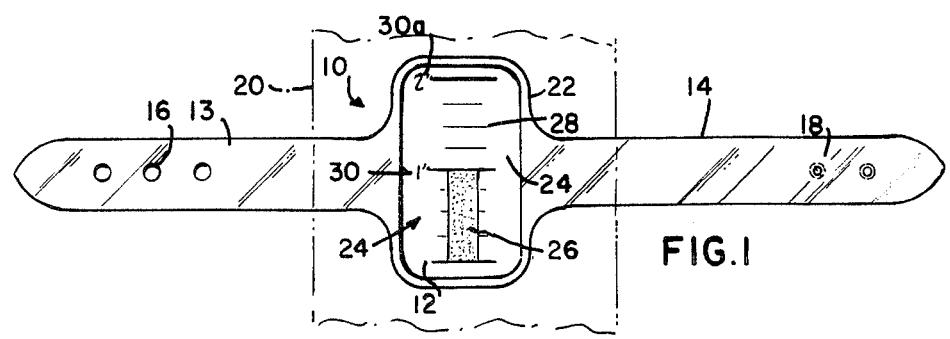
FIG. 1 is a bottom view illustrating a therapeutic device of the present invention.

Referring now more particularly to FIGS, 1, 2 and 3 of the drawing, there is illustrated generally at 10 an embodiment of a therapeutic device of the present invention. The device 10 comprises an inner supporting member 12 having two elongated flexible members 13 and 14. Flexible member 13 is provided with holes 16 adapted to co-act by press fit with projections 18 carried by flexible member 14 to secure the device circumferentially about (for example) the wrist 20, of the recipient user.

Figure 2:
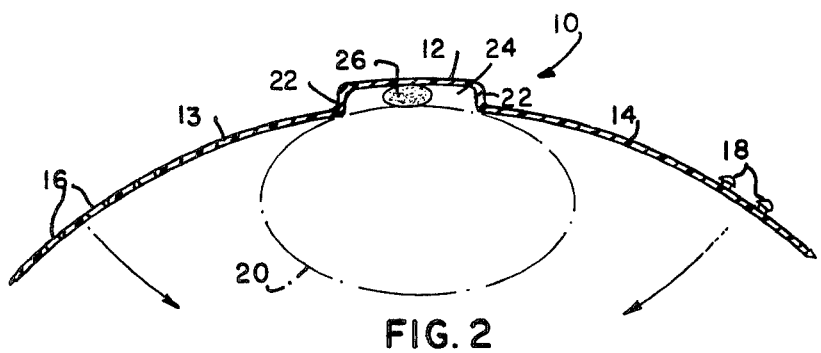
FIG. 2 is a side cross-sectional view of the therapeutic device of FIG. 1.
Figure 3:
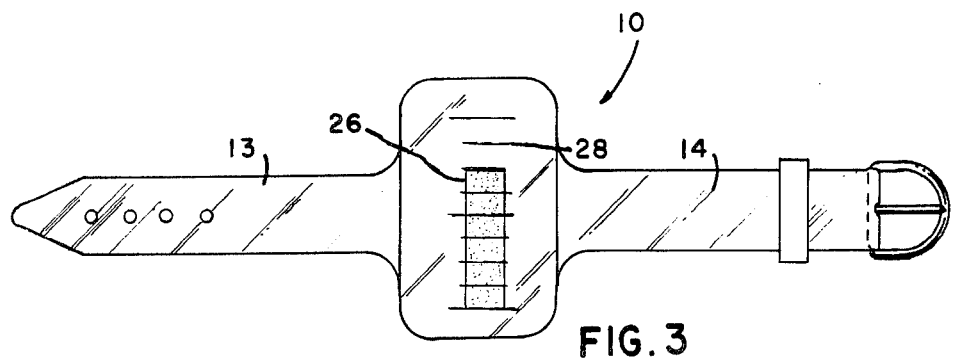
FIG. 3 is a top view of the therapeutic device of FIG. 1, except that it illustrates a modified embodiment of attachment.

The inner support member 12 is provided with walls 22 defining a reservoir or chamber 24 for receiving a therapeutic material. For explanation and illustration purposes, a therapeutic medicament such as may be extruded or squeezed from a tube is illustrated at 26 (as best shown in FIG. 1 and FIG. 2). Disposed upon the inner surface of support member 12 are indicia of measurement comprising lines 28 and numerals 30 and 30a dividing the inner surface of the support member 12 into inches and fractions thereof. The indicia of measurement can then be employed by the user to measure a predetermined amount of therapeutic medicament to be used and deposited in support member 12. In the preferred embodiment, the support member 12 and flexible members 13 and 14 are formed of a plastic material. As illustrated, the support member 12 may be formed of a transparent plastic material to permit the recipient user to observe the quantity of therapeutic medicament remaining from time to time. As illustrated by FIGS. 1–4 of the drawing the top support member 12 and side walls 22 cooperate to provide the chamber of the inner support member with a structure which is less flexible than the elongated flexible members 13 and 14.

Figure 4:
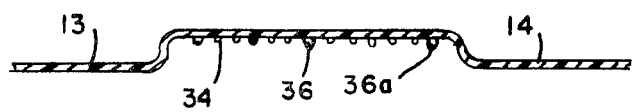
FIG. 4 is a side fragmentary view of the therapeutic device of FIG. 1 illustrating a modified form of indicia of measurement.

Referring now to FIG. 4 of the drawing, there is illustrated a modified support member having indicia of measurement comprising a plurality of spaced, raised members 34 instead of lines 28 of FIG. 1. The higher raised members 36 and 36a represent, for example, an inch and two inches of measure. Such raised members 36, 36a are particularly suitable for measurement by recipient users of limited eyesight.

Figure 5:
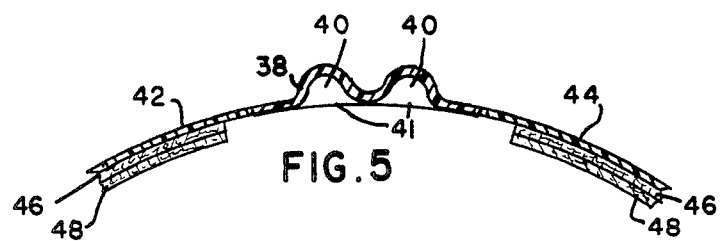
FIG. 5 is a side cross-sectional view of another embodiment of the invention.
Figure 6:
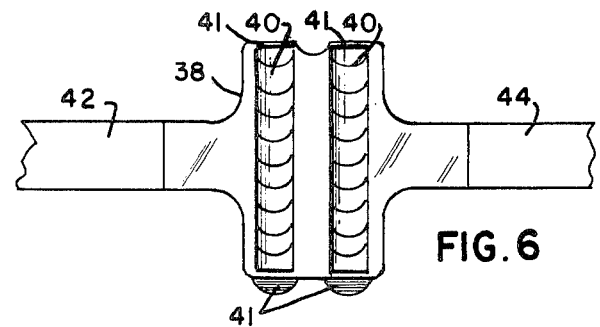
FIG. 6 is a bottom fragmentary view of the therapeutic device of FIG. 5.

Referring now to FIGS. 5 and 6, there is illustrated a modified embodiment of the therapeutic device of the invention. The device illustrated comprises a support member 38 having two channels or grooves 40 to receive the therapeutic material which may be the same or different medicament material. The device is provided with elongated flexible members 42 and 44 provided with a conventional pressure sensitive adhesive material 46, having a conventional removable protective strip 48. The channels 40 are preferably provided with channel end walls 41 to confine the medicament within the channels. The plurality of channels or grooves as illustrated in FIGS. 5 and 6 are particularly suitable where the recipient requires treatment with more than one kind of medicament.

Figure 7:
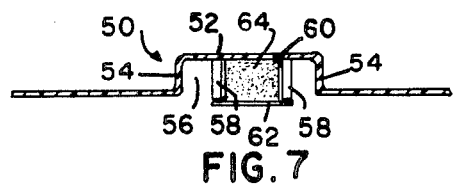
FIG. 7 is a partially fragmentary, partially cross-sectional view of the modified form of the therapeutic device of FIG. 1.
Figure 8:
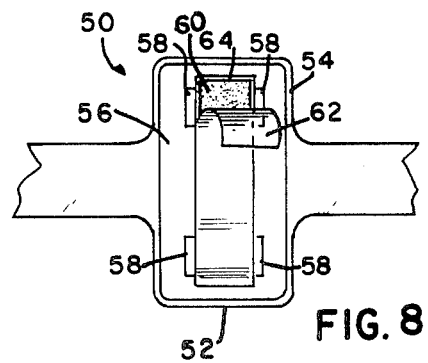
FIG. 8 is a fragmentary bottom view of the therapeutic device of FIG. 7.

Referring now to FIGS. 7 and 8, there is illustrated still another modified embodiment of the support member of the therapeutic device of the invention.

The support member 50 comprises a base member 52 and walls 54, defining a chamber 56. Disposed on base member 52 are resilient holding means 58 for releasibly holding a container 60 of medicament. The container 60 is preferably provided with a removable foil 62 to expose the medicament material 64 to the environment of use. Suitable flexible means such as, for example, 42 and 44 (as described in FIGS. 1, 3 and 5) may be employed to hold the support member 50 and therapeutic medicament material 64 adjacent the environment of use.

While the invention has been described with respect to preferred embodiments, it will be apparent to those skilled in the art that changes and modifications may be made without departing from the scope of the invention herein involved in its broader aspects. Accordingly, it is intended that all matter contained in the above description, or shown in the accompanying drawing shall be interpreted as illustrated and not in limiting sense.

What is claimed is:

1. A therapeutic device adapted to receive a therapeutic material and maintain said material in contact with the external body skin of a recipient to promote absorption of said material through said skin comprising an integral structure having an inner support member and laterally extending flexible elongated outer members, the inner support member comprising a top support member having a substantially flat inner surface and side walls disposed about the inner surface of said top support member defining a chamber to receive and hold a quantity of therapeutic material therein, said top support member and said side walls cooperating to provide said chamber with a structure having less flexibility than said elongated outer members, said side walls having height with respect to the said inner surface of said inner support member to provide said chamber with sufficient depth whereby at least the lower surface of said therapeutic material is maintained in contact with said body skin, means disposed on said inner surface of said top support member for detecting when a predetermined amount of therapeutic material has been deposited upon said inner surface comprising a plurality of spaced raised members, indicia of measurement associated with said spaced raised members, and means disposed on said outer flexible elongated portions for securing said therapeutic device to said recipient.

* * * * *